US010752559B2

(12) United States Patent
Potthoff et al.

(10) Patent No.: US 10,752,559 B2
(45) Date of Patent: Aug. 25, 2020

(54) UREA-CONTAINING FERTILIZERS AND PROCESS FOR PRODUCTION THEREOF

(71) Applicants: UHDE FERTILIZER TECHNOLOGY B.V., Roermond (NL); THYSSENKRUPP AG, Essen (DE)

(72) Inventors: Matthias Potthoff, Dortmund (DE); Thomas Krawczyk, Wuppertal (DE); Harald Franzrahe, Dortmund (DE); Luc Albert Vanmarcke, Lembecke (BE)

(73) Assignees: THYSSENKRUPP FERTILIZER TECHNOLOGY GMBH, Dortmund (DE); THYSSENKRUPP AG, Essen (DE)

( * ) Notice: Subject to any disclaimer, the term of this patent is extended or adjusted under 35 U.S.C. 154(b) by 257 days.

(21) Appl. No.: 16/062,048

(22) PCT Filed: Dec. 17, 2016

(86) PCT No.: PCT/EP2016/081626
§ 371 (c)(1),
(2) Date: Jun. 13, 2018

(87) PCT Pub. No.: WO2017/103243
PCT Pub. Date: Jun. 22, 2017

(65) Prior Publication Data
US 2018/0370865 A1    Dec. 27, 2018

(30) Foreign Application Priority Data

Dec. 17, 2015 (DE) .................. 10 2015 122 070

(51) Int. Cl.

| | | |
|---|---|---|
| C05D 9/00 | (2006.01) | |
| C05C 3/00 | (2006.01) | |
| C05C 9/00 | (2006.01) | |
| A23K 50/15 | (2016.01) | |
| C05G 3/20 | (2020.01) | |
| C05G 5/12 | (2020.01) | |
| B01J 2/16 | (2006.01) | |
| A23K 40/10 | (2016.01) | |
| A23K 20/10 | (2016.01) | |
| B01J 2/02 | (2006.01) | |
| C01C 1/24 | (2006.01) | |
| C07C 47/12 | (2006.01) | |
| C07C 55/02 | (2006.01) | |
| C07C 55/22 | (2006.01) | |
| C08L 29/04 | (2006.01) | |
| C08L 39/02 | (2006.01) | |
| C08L 79/02 | (2006.01) | |

(52) U.S. Cl.
CPC .............. *C05C 9/005* (2013.01); *A23K 20/10* (2016.05); *A23K 40/10* (2016.05); *A23K 50/15* (2016.05); *B01J 2/02* (2013.01); *B01J 2/16* (2013.01); *C05C 3/005* (2013.01); *C05D 9/00* (2013.01); *C05G 3/20* (2020.02); *C05G 5/12* (2020.02); *C01C 1/24* (2013.01); *C07C 47/12* (2013.01); *C07C 55/02* (2013.01); *C07C 55/22* (2013.01); *C08L 29/04* (2013.01); *C08L 39/02* (2013.01); *C08L 79/02* (2013.01)

(58) Field of Classification Search
None
See application file for complete search history.

(56) References Cited

U.S. PATENT DOCUMENTS

| 4,219,589 | A | 8/1980 | Goethals | |
|---|---|---|---|---|
| 5,766,302 | A | 6/1998 | Lefroy | |
| 2004/0009878 | A1 | 1/2004 | Lynch | |
| 2007/0245786 | A1 | 10/2007 | Brosse | |
| 2016/0368832 | A1* | 12/2016 | Ringold | .................. C05C 9/005 |
| 2017/0158575 | A1* | 6/2017 | Schneider | .............. C09K 15/06 |

FOREIGN PATENT DOCUMENTS

| DE | 19642761 A | 4/1998 |
|---|---|---|
| EP | 0533024 A | 3/1993 |
| FR | 1021100 A | 2/1953 |
| FR | 2874008 A | 2/2006 |
| JP | 52-016362 A | 2/1977 |
| JP | 56109888 A | 7/1981 |
| JP | 11228274 A | 8/1999 |
| JP | 2012509833 A | 4/2012 |
| JP | 2013521213 A | 6/2013 |
| WO | 2006/091077 A | 8/2006 |
| WO | 2006091007 A | 8/2006 |
| WO | 2010060535 A | 6/2010 |
| WO | 2011071909 A | 6/2011 |
| WO | 2013035106 A | 3/2013 |
| WO | 2015026806 A | 2/2015 |
| WO | 2015193377 A | 12/2015 |

OTHER PUBLICATIONS

English Translation of International Search Report issued in PCT/EP2016/081626, dated Feb. 14, 2017 (dated Apr. 28, 2017).
ISO 3944 [In the process of locating copy.].
Rutland, IFDC S-112, Bulk-Density (Tapped), Manual for Determining Physical Properties of Fertilizer, Feb. 1993.
Rutland, IFDC S-116, Abrasion Resistance (Rotary-Drum Method) Manual for Determining Physical Properties of Fertilizer, Feb. 1993.

(Continued)

*Primary Examiner* — Wayne A Langel
(74) *Attorney, Agent, or Firm* — thyssenkrupp North America, LLC

(57) ABSTRACT

A particulate, urea-containing composition and use of an additive for producing a particulate, urea-containing composition and methods of producing a particulate, urea-containing composition.

18 Claims, No Drawings

(56) References Cited

OTHER PUBLICATIONS

Rutland, IFDC S-115, Granule Crushing Strength, Manual for Determining Physical Properties of Fertilizer, Feb. 1993.
Rutland, IFDC S-106, Caking Tendency (Small-Bag Method), Manual for Determining Physical Properties of Fertilizer, Feb. 1993.
ISO 3944, Fertilizers—Determination of bulk density (loose), Third Edition, (1992).

* cited by examiner

UREA-CONTAINING FERTILIZERS AND PROCESS FOR PRODUCTION THEREOF

CROSS REFERENCE TO RELATED APPLICATIONS

This application is a U.S. National Stage Entry of International Patent Application Serial Number PCT/EP2016/081626, filed Dec. 17, 2016, which claims priority to German Patent Application No. DE 10 2015 122 070.9, filed Dec. 17, 2015, the entire contents of both of which are incorporated herein by reference.

FIELD

The present disclosure generally relates to a particulate, urea-containing composition and to the use of an additive for producing a particulate, urea-containing composition.

BACKGROUND

There are a variety of methods known in the prior art for producing particulate, urea-containing compositions. In the past, urea particles have been produced customarily by means of spray crystallization, where a substantially water-free urea melt (water content from 0.1 to 0.3 wt %) is sprayed from the upper part of a spray crystallization tower into an ascending stream of air at ambient temperature, with the droplets solidifying to form crystals (prills). The diameters of the resultant prills are relatively small, and their mechanical strength is low.

Further known methods for producing particulate, urea-containing compositions use drum or plate granulating units, or else what are called spherodizer drums, for producing the particles.

Urea particles having larger particle diameters and better mechanical properties are nowadays usually produced by granulation of a substantially water-free urea melt or of an aqueous urea solution in a fluidized bed, as described for example in U.S. Pat. No. 4,219,589. In these granulation methods, an aqueous urea solution having a urea concentration of 70-99.9 wt % is introduced, in the form of very finely dispersed droplets having an average diameter of 20-120 μm, into a fluidized bed of urea particles, the temperature being selected such that the water in the solution sprayed onto the urea particles undergoes evaporation and urea is deposited on the particles, thus producing granules having a desired particle size of 2.5 mm or more.

Because this method produces relatively large quantities of fine dust, particularly if the urea solution used has a water content of more than 5 wt %, it is common to employ granulating additives which reduce this dusting. The result of adding these additives is that the granular particles and particularly their surface remain plastic, meaning that round particles having a smooth surface and good mechanical stability are obtained as a result of their rolling movements and collisions.

The resulting granules therefore have high compressive strength and impact resistance, a low tendency toward dusting through abrasion, and also, even on prolonged storage, only a low tendency toward caking. Such granulating additives are employed, however, not only in fluidized bed granulation, but also in other methods referred to above.

Granulating additives employed are customarily formaldehyde or water-soluble adducts and/or condensation products of formaldehyde and urea, but must be added in relatively large quantities and have toxicity properties which render their handling not unproblematic. Formaldehyde emissions pose an acute risk to health and environment, although the introduction of urea-formaldehyde prepolymers such as UF80 or UF85 has reduced such risks. Moreover, the issue of health risks also arises in connection with chronic exposure to formaldehyde vapors, which cannot be avoided entirely even by the use of such prepolymers.

A further problem affecting the granulation of urea-containing particles is the production of dust, referring here to particles having a diameter of less than 0.5 mm. This production of dust is attributable substantially to three sources. A first is the abrasion of the granules owing to movements and collisions of the particles, in the fluidized bed, for example, with the amount of dust produced being substantially dependent on the mechanical properties of the granules. Furthermore, the nozzles or the liquid distributors used in the other methods each generate drops with a certain distribution of diameters, with the finest drops then solidifying before they strike the urea particles, meaning that the dust thus formed leaves the granulator again with the outgoing air. Lastly, a third source is the dust resulting from the comminution of oversized granular particles, this dust customarily being transferred directly into the granulator again in the methods and units according to the prior art. 10 to 20 wt % of the comminuted particles have a diameter of less than 1 mm, and a large fraction of this is dust. Accordingly, this fraction of comminuted particles means that 1% to 1.5% of dust is returned to the granulator per metric ton of end product, and 3-5% of the total dust per metric ton of end product from an industrial unit is attributable to the granulator.

In order to avoid or reduce the disadvantages identified above, various alternatives to formaldehyde and its water-soluble adducts and/or condensation products have been investigated, but in each case are also hampered by restrictions and/or disadvantages.

Reference may be made, for example, to the use of alkali metal lignosulfonates, as described in U.S. Pat. No. 5,766,302, or to the use of glyoxal or carbohydrates. In the resulting urea product, and depending on the production method, however these alternatives lead to a yellowish or brownish discoloration, which in many cases is undesirable. On the other hand, the use of surface-active substances such as, for example, mixtures of polyvinyl acetate and polyvinyl alcohol as granulating additives likewise leads to problems, since these additives have a tendency to foam, as for example when the additive is mixed with the melt or in the scrubbers where the treated urea dust is dissolved and impacts the efficiency of the scrubbers. The tendency of these substances to form foam also has consequences for the end product, moreover, this product having a relatively low density and being rejected by the market. Overall, therefore, any tendency toward foaming on industrial application of the urea granules is unacceptable.

Thus a need exists for a method for producing particulate, urea-containing compositions, wherein the disadvantages of the prior art are eliminated or at least diminished.

DETAILED DESCRIPTION

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting 'a' element or 'an' element in the appended claims does not restrict those claims to articles, apparatuses, systems, methods, or the like having only one of that element, even where other elements in the same claim or different claims are preceded by 'at least one' or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

The disclosure relates to a particulate, urea-containing composition and to the use of an additive for producing a particulate, urea-containing composition.

It has surprisingly been found that using particular additives it is possible to obtain a urea-containing, particulate composition having satisfactory properties, without the use of formaldehyde and urea-formaldehyde condensates. In particular it is possible in this way

- to avoid the health and environmental risks associated with the use of formaldehyde and urea-formaldehyde condensates; and/or
- to provide a more cost-effective alternative to the production of the compositions, relative to compositions produced using formaldehyde and urea-formaldehyde condensates; and/or
- to reduce or even avoid completely the unwanted coloring of the composition; and/or
- to reduce or even avoid entirely the unwanted foaming during production or during wet scrubbing; and/or
- to achieve particle growth comparable with that when using formaldehyde and urea-formaldehyde condensates; and/or
- to reduce or even avoid entirely the formation of dust during the production of the composition; and/or
- to produce a particulate composition whose particles, in comparison to compositions produced using formaldehyde and urea-formaldehyde condensates, have properties which are at least comparable or are even better, especially with regard to mechanical properties such as, for example, compressive strength, impact resistance, low tendency toward abrasion or toward caking, particularly on prolonged storage.

One aspect of the invention relates to a particulate composition comprising
(i) urea;
and an additive comprising one or both of components (ii) and (iii):
(ii) combination of at least one oligomer or polymer containing amino groups and of at least one functionalized polyvinyl compound;
(iii) at least one aliphatic $C_2$-$C_8$ dialdehyde;
and an adjuvant comprising one or more of components (iv) to (vi):
(iv) sulfur;
(v) ammonium sulfate;
(vi) at least one trace element;
wherein the weight fraction of component (i) is >10 wt % and the weight fraction of the sum of components (ii) and (iii) in the composition is <1 wt %.

A further aspect of the invention relates to a particulate composition comprising
(i) urea;
and an additive comprising one or both of components (ii) and (iii):
(ii) combination of at least one oligomer or polymer containing amino groups and of at least one functionalized polyvinyl compound;
(iii) at least one aliphatic $C_2$-$C_8$ dialdehyde;
and an adjuvant comprising one or more of components (iv) to (vi):
(iv) sulfur;
(v) ammonium sulfate;
(vi) at least one trace element
wherein the weight fraction of component (i) is >50 wt %, the weight fraction of components (iv) and (v) as individual component or in the composition is <50 wt %, and the weight fraction of component (vi) is <5 wt % and the weight fraction of the sum of components (ii) and (iii) in the composition is <1 wt %.

In one preferred embodiment, the weight fraction of component (i) in the particulate composition is >30 wt %, more preferably 50 wt %, more preferably still >60 wt %, very preferably >70 wt %, especially preferably >80 wt %, more preferably still >96 wt %.

The weight fraction of the sum of components (ii) and (iii) in the particulate composition is preferably <1 wt %, more preferably <0.8 wt %, more preferably still <0.6 wt %, very preferably <0.4 wt % and especially <0.2 wt %.

Where the adjuvant to the particulate composition comprises only component (iv), the weight fraction of component (iv) in the particulate composition is preferably <50 wt %, more preferably <40 wt %, more preferably still <30 wt %, very preferably <20 wt % and especially <10 wt %. Where the adjuvant to the particulate composition comprises only component (iv), the weight fraction of component (iv) in the particulate composition is preferably in the range from 1 to 30 wt %, more preferably in the range from 2 to 20 wt % and especially in the range from 3 to 10 wt %.

Where the adjuvant to the particulate composition comprises only component (v), the weight fraction of component (v) in the particulate composition is preferably <50 wt %, more preferably <40 wt %, more preferably still <30 wt %, very preferably <20 wt % and especially <10 wt %.

Where the adjuvant to the particulate composition comprises both component (iv) and component (v), the weight fraction of the sum of components (iv) and (v) in the particulate composition is <50 wt %, more preferably <40 wt %, more preferably still <30 wt %, very preferably <20 wt % and especially <10 wt %.

Where the adjuvant to the particulate composition comprises component (vi), the weight fraction of component (vi) in the particulate composition is preferably <5 wt %, more preferably <4 wt %, more preferably still <3 wt %, very preferably <2 wt % and especially <1 wt %.

Oligomers and polymers comprising amino groups that are employed in accordance with the invention comprise, in particular, polymers and oligomers having a molecular weight (MW) of 250 to 2 000 000, of 300 to 2 000 000, of 350 to 2 000 000, of 400 to 2 000 000, of 450 to 2 000 000, of 500 to 2 000 000, of 550 to 2 000 000, of 600 to 2 000 000, of 650 to 2 000 000, of 700 to 2 000 000, of 750 to 2 000 000, of 800 to 2 000 000, of 850 to 2 000 000, of 900 to 2 000 000, of 950 to 2 000 000, of 1000 to 2 000 000, of 1050 to 2 000 000, of 1100 to 2 000 000, of 1150 to 2 000 000, and of 1200 to 2 000 000 daltons.

For example, the oligomers and polymers comprising amino groups and employed in accordance with the invention may have a molecular weight (MW) of 500 to 1 000 000, of 550 to 1 000 000, of 600 to 1 000 000, of 650 to 1 000 000, of 700 to 1 000 000, of 750 to 1 000 000, of 800 to 1 000 000, of 850 to 1 000 000, of 900 to 1 000 000, of 950 to 1 000 000, of 1000 to 1 000 000, of 1050 to 1 000 000, of 1100 to 1 000 000, of 1150 to 1 000 000, and also of 1200 to 1 000 000 daltons, or in the range from 500 to 10 000, from 550 to 10 000, from 600 to 10 000, from 650 to 10 000, from 700 to 10 000, from 750 to 10 000, from 800 to 10 000, from 850 to 10 000, from 900 to 10 000, from 950 to 10 000, from 1000 to 10 000, from 1050 to 10 000, from 1100 to 10 000, from 1150 to 10 000, and also from 1200 to 10 000 daltons.

The oligomers and polymers containing amino groups may preferably have a nitrogen content of 10 to 50 wt %, based on the weight of the polymer or oligomer, and contain primary, secondary or tertiary amino groups which independently of one another contain alkyl or arylalkyl groups, as for example $C_{1-6}$ alkyl or aryl-$C_{1-3}$ alkyl, where aryl in particular may be phenyl or pyridyl, which may be unsubstituted or substituted optionally by 1, 2, 3, 4 or 5 substituents independently of one another selected from the group consisting of F, Cl, Br, $CF_3$, $C_{1-6}$ alkyl, $C_{1-6}$ alkoxy, $NH_2$, $C_{1-6}$ alkylamino and di($C_{1-6}$ alkyl)amino.

Examples contemplated as oligomers and polymers containing amino groups include polyamines, polymeric polyamines, nitrogen-substituted vinyl polymers, polyoxazolines, polypropyleneimine and its dendrimers, polyethyleneimine and its dendrimers, polyamidoamine and its dendrimers, and also copolymers and derivatives and combinations of two or more of the stated substances.

Preferred oligomers and polymers containing amino groups comprise polyamines and polymeric polyamines, polyalkyleneimines such as, for example, polyethyleneimines and polypropyleneimines, polyvinylamines, polyalkoxylated polyamines, ethoxylated polyamines, propoxylated polyamines, alkylated and benzylated polyamines, and also combinations of two or more of the aforementioned components.

Especially preferred for use as oligomers and polymers containing amino groups are polyethyleneimines, polyethyleneimine dendrimers, and also their copolymers, derivatives and mixtures of at least two of these components.

Suitable polyethyleneimines may comprise linear or branched polyethyleneimine polymers or oligomers having, for example, 10 or more monomer units and also their derivatives, analogs, copolymers and mixtures of at least two of these components.

Polyethyleneimines may be obtained by the polymerization of ethyleneimine and are available commercially on the market, in the form, for example, of the Lupasol® and Epomin® product families, including more particularly the products Lupasol® G20, Lupasol® FG, Lupasol® G35, Lupasol® P, and Lupasol®1595 (the Lupasol® products are available from BASF (Florham Park, N.J., USA)), and also Epomin® SP-003, Epomin® SP-006, Epomin® SP-012, Epomin® SP-018, Epomin® SP-200, Epomin® SP-1000, and Epomin® SP-1050 (the Epomin® products are available from Nippon Shokubai (Osaka, Japan)).

Functionalized polyvinyl compounds contemplated in accordance with the invention are more particularly compounds based on the repeating unit $(CHXCHY)_n$, in which X is selected from the group consisting of H, $NH_2$, OH, COOH, COR, $CONH_2$, $CH_2NH_2$, $CH_2NHR$, $CH_2OH$ and $CH_2OR$ and Y is selected from the group consisting of $NH_2$, OH, COOH, COR, $CONH_2$, $CH_2NH_2$, $CH_2NHR$, $CH_2OH$ and $CH_2OR$ and where R independently at each occurrence may be alkyl, especially $C_{1-6}$ alkyl, or aryl, especially phenyl or pyridyl, which may be unsubstituted or substituted optionally by 1, 2, 3, 4 or 5 substituents independently of one another selected from the group consisting of F, Cl, Br, $CF_3$, $C_{1-6}$ alkyl, $C_{1-6}$ alkoxy, $NH_2$, $C_{1-6}$ alkylamino and di($C_{1-6}$ alkyl)amino.

The functionalized polyvinyl compounds employed in accordance with the invention may for example a molecular weight (MW) of 250 to 2 000 000, of 300 to 2 000 000, of 350 to 2 000 000, of 400 to 2 000 000, of 450 to 2 000 000, of 500 to 2 000 000, of 550 to 2 000 000, of 600 to 2 000 000, of 650 to 2 000 000, of 700 to 2 000 000, of 750 to 2 000 000, of 800 to 2 000 000, of 850 to 2 000 000, of 900 to 2 000 000, of 950 to 2 000 000, of 1000 to 2 000 000, of 1050 to 2 000 000, of 1100 to 2 000 000, of 1150 to 2 000 000, and also of 1200 to 2 000 000 daltons.

The functionalized polyvinyl compound contemplated is preferably polyvinyl alcohol or polyvinylamine or a mixture thereof. With particular preference the functionalized polyvinyl compound is a polyvinylamine.

The polyvinylamine and the polyvinyl alcohol may each preferably have a molecular weight (MG) of 500 to 1 000 000, of 550 to 1 000 000, of 600 to 1 000 000, of 650 to 1 000 000, of 700 to 1 000 000, of 750 to 1 000 000, of 800 to 1 000 000, of 850 to 1 000 000, of 900 to 1 000 000, of 950 to 1 000 000, of 1000 to 1 000 000, of 1050 to 1 000 000, of 1100 to 1 000 000, of 1150 to 1 000 000, and also of 1200 to 1 000 000 daltons or in the range from 500 to 10 000, from 550 to 10 000, from 600 to 10 000, from 650 to 10 000, from 700 to 10 000, from 750 to 10 000, from 800 to 10 000, from 850 to 10 000, from 900 to 10 000, from 950 to 10 000, from 1000 to 10 000, from 1050 to 10 000, from 1100 to 10 000, from 1150 to 10 000, and also from 1200 to 10 000 daltons.

Suitable polyvinylamines include, in particular, linear polymers and copolymers which derive from vinylformamide monomers and may comprise cationic and anionic polyvinylamine copolymers and also charged and protonated polyvinylamines.

Suitable polyvinylamines are available commercially on the market, examples being those of the Lupamin® product family, including more particularly the products Lupamin® 1595, Lupamin® 4500, Lupamin® 5095, Lupamin® 9030, Lupamin® 9050 and Lupamin® 9095. Examples of cationic and anionic polyvinylamine copolymers are those of the Luredur® product family, including more particularly the products Luredur® Am na, Luredur® AV, Luredur® VH, Luredur® VI, Luredur® VM, Luredur® PR8094, Luredur® PR8261, and Luredur® PR8349. Examples of charged or protonated polyvinylamines are products of the Catiofast® product series, including more particularly the products Catiofast® GM, Catiofast® PL, Catiofast® PR8236, Catiofast® VCB, Catiofast® VFH, Catiofast® VLW, Catiofast® VMP and Catiofast® VSH. The Lupamin®, Luredur®, and Catiofast® products are available from BASF (Florham Park, N.J., USA).

The skilled person understands that the combination as per (ii) should be understood in particular as comprising the combination of at least one oligomer or polymer containing amino groups, as a first component of the combination, and of at least one functionalized polyvinyl compound, as a second component of the combination.

Employed as component (iii) of the invention are linear or branched aliphatic $C_2$-$C_8$ dialdehydes. Contemplated with preference as additive component (iii) is ethanedial or glutaraldehyde, more preferably glutaraldehyde.

Unless otherwise indicated, the weight figures (wt %) specified in connection with the particulate composition refer in each case always to the total weight of the particulate composition. The skilled person recognizes that the specified components and weight figures need not be fulfilled for any arbitrarily small sub-quantity of the particles, but instead are fulfilled on average over a representative amount of the particles produced.

The particulate composition of the invention may comprise further constituents as well as the stated constituents. The nature of the constituents and also the amount thereof are dependent, for example, on the component (i) used. Hence the particulate composition of the invention may comprise water, in an amount, for example, of 0.05 to 0.5 wt %, more particularly 0.1 to 0.3 wt %, and by-products of urea synthesis such as biuret or $NH_3$, for example. The fraction of the by-products is customarily not more than 1.5 wt %, more particularly not more than 1.25 wt %.

In one preferred embodiment the particulate composition comprises, as component (vii) of the additive, at least one compound selected from the group of aliphatic dicarboxylic acids, their salts and anhydrides, aliphatic tricarboxylic acids, their salts and anhydrides, aromatic dicarboxylic acids, their salts and anhydrides, and also aldehydic acids, their salts and anhydrides, where preferably the weight fraction of component (i) is >60 wt % and the weight fraction of the sum of components (ii), (iii) and (vii) in the composition is <1 wt %.

The adjuvant may comprise either only sulfur or only ammonium sulfate or only at least one trace element. The adjuvant may likewise comprise all possible combinations of the stated components. The sulfur may be used either elementally or else as a constituent of a compound. For example, the adjuvant may comprise sulfur in the form of sulfates. Elements referred to as trace elements are preferably those which are necessary for a living entity and which occur customarily in mass fractions of less than 50 mg/kg in an organism. Trace elements may comprise, for example, boron, chlorine, iron, copper, manganese, molybdenum and/or zinc. A skilled person recognizes that the term "trace element" embraces not only one individual element but also any possible mixture of two or more elements.

In one preferred embodiment the components of the particulate composition are homogeneously mixed. To mix the urea present in the particulate composition optionally with sulfur, additional auxiliaries may be necessary in order to form a stable emulsion. Suitable methods for forming an emulsion of sulfur and urea are known to a skilled person. Also known to a skilled person are the process steps that may be necessary for the mixing of the urea and ammonium sulfate.

The skilled person recognizes that the components (ii), (iii), (iv), (v), (vi) and (vii) employed may undergo partial or even complete interaction optionally with one another and optionally also with the urea component (i) during the production of the particulate composition. Known examples include the crosslinking, with formation of covalent bonds, for aldehydes and/or carboxylic anhydrides with urea, or the formation of complexes of urea and carboxylic acids. Components such as polyvinyl alcohol and polyvinylamine, for example, tend toward the formation of hydrogen bonds. In the end product obtained, therefore, the components employed in producing the particulate composition may optionally be present in partly or completely modified form. Such modified components are also embraced by the invention.

In one particularly preferred embodiment, the particulate composition of the invention comprises
urea;
and an additive comprising component (ii) and one or both of components (iii) and (vii):
(ii) combination of polyethyleneimine and polyvinyl alcohol or combination of polyethyleneimine and polyvinylamine;
(iii) at least one aliphatic $C_2$-$C_8$ dialdehyde;
(vii) at least one compound selected from the group of aliphatic dicarboxylic acids, their salts and anhydrides, aliphatic tricarboxylic acids, their salts and anhydrides, aromatic dicarboxylic acids, their salts and anhydrides, and aldehydic acids, their salts and anhydrides;
and an adjuvant comprising one or more of components (iv) to (vi):
(iv) sulfur;
(v) ammonium sulfate;
(vi) at least one trace element;
wherein preferably the weight fraction of component (i) is >50 wt % and the weight fraction of the sum of components (ii), (iii) and (vii) in the composition is <1 wt % and the weight fraction of the sum of components (iv), (v) and (vi) in the composition is <50 wt %.

If the composition of the invention includes an aliphatic dicarboxylic acid as component (vii), the latter may preferably be selected from the group consisting of oxalic acid, malonic acid, succinic acid, glutaric acid, adipic acid, pimelic acid, suberic acid, azelaic acid, sebacic acid, undecanedioic acid, dodecanedioic acid, tridecanedioic acid, tetradecanedioic acid, hexadecanedioic acid, and also each of their salts and anhydrides. A particularly preferred dicarboxylic acid of component (vii) present is oxalic acid, succinic acid or a mixture of these two acids.

If the composition of the invention includes an aliphatic tricarboxylic acid as component (vii), the latter may preferably be selected from the group consisting of citric acid, isocitric acid, and also each of their salts and anhydrides. A particularly preferred tricarboxylic acid of component (vii) present is citric acid.

Where the composition of the invention includes an aromatic dicarboxylic acid or anhydride thereof as component (vii), the latter may preferably be selected from the group consisting of phthalic acid, phthalic anhydride, isophthalic acid and terephthalic acid. A particularly preferred aromatic dicarboxylic acid of component (vii) and/or anhydride thereof present is phthalic acid, phthalic anhydride or a mixture thereof.

If the composition of the invention includes an aldehydic acid as component (vii), the latter is preferably glyoxylic acid.

If one acids of component (vii) is in the form of its salt, those contemplated in particular are salts of the alkali metals such as, for example, sodium and potassium and of the alkaline earth metals such as, for example, calcium and magnesium, but also ammonium salts, especially of the type $[NH_xR_{4-x}]^+$, in which x=0, 1, 2, 3 or 4 and R is a linear or branched $C_{1-4}$ alkyl radical.

In a further preferred embodiment, the particulate composition comprises
(i) urea;
and an additive comprising component (ii) and one or both of components (iii) and (vii):
(ii) combination of polyethyleneimine and polyvinylamine;
(iii) ethanedial and/or glutaraldehyde;
(vii) at least one compound selected from the group consisting of oxalic acid, succinic acid, citric acid, phthalic acid, phthalic anhydride, glyoxylic acid and salts thereof,
and an adjuvant comprising one or more of components (iv) to (vi):
(iv) sulfur;
(v) ammonium sulfate;
(vi) at least one trace element;
wherein preferably the weight fraction of component (i) is >50 wt % and the weight fraction of the sum of components (ii), (iii) and (vii) in the composition is <1 wt % and the weight fraction of the sum of components (iv), (v) and (vi) in the composition is <50 wt %.

Especially preferred embodiments of the particulate composition comprise
(i) urea;
and an additive selected from the group (a)-(i)
(a) additive comprising (ii) a combination of polyethyleneimine and polyvinylamine;
(b) additive comprising (iii) glutaraldehyde;
(c) additive comprising (ii) a combination of polyethyleneimine and polyvinylamine and (vii) oxalic acid;
(d) additive comprising (ii) a combination of polyethyleneimine and polyvinylamine and (vii) citric acid;
(e) additive comprising (ii) a combination of polyethyleneimine and polyvinylamine and (vii) succinic acid;
(f) additive comprising (ii) a combination of polyethyleneimine and polyvinylamine and (vii) phthalic acid;
(g) additive comprising (ii) a combination of polyethyleneimine and polyvinylamine and (vii) phthalic anhydride;
(h) additive comprising (ii) a combination of polyethyleneimine and polyvinylamine and (vii) glutaraldehyde;
(i) additive comprising (ii) a combination of polyethyleneimine and polyvinylamine and (vii) glyoxylic acid;
and an adjuvant comprising one or more of components (iv) to (vi):
(iv) sulfur;
(v) ammonium sulfate;
(vi) at least one trace element;
where preferably the weight fraction of component (i) is >50 wt % and the weight fraction of the sum of components (ii), (iii) and (vii) in the composition is <1 wt % and the weight fraction of the sum of components (iv), (v) and (vi) in the composition is <50 wt %.

The weight fraction of component (i) in the particulate composition is preferably >50 wt %, more preferably >60 wt %, very preferably >96 wt %.

The weight fraction of the additive component may vary, depending for example on components (ii), (iii) and (vii) used. The weight fraction of the sum of components (ii), (iii) and (vii) in the particulate composition is preferably <0.5 wt %, more preferably <0.4 wt %, very preferably <0.3 wt % and even more preferably <0.25 wt %.

If the additive component comprises two or more components, the relative fractions thereof may also vary. Thus, for example, the weight ratio of components (ii) and (iii) or the weight ratio of components (ii) and (vii) may be in the range from 1:20 to 20:1, preferably from 1:15 to 15:1, more preferably 1:10 to 10:1, and may comprise incremental values in between.

Especially preferred embodiments of the particulate composition comprise a combination of polyethyleneimine and polyvinylamine. The weight ratio of polyethlyeneimine and polyvinylamine within the combination of these two components may vary, in the range, for example, from 1:20 to 20:1, preferably from 1:15 to 15:1, more preferably 1:10 to 10:1, and may comprise incremental values in between.

Furthermore, the weight ratio of the combination of the two components polyethlyeneimine and polyvinylamine to component (iii), or the weight ratio of the combination of the two components polyethlyeneimine and polyvinylamine to component (vii), may also vary and in each case may comprise, for example, in the range from 1:20 to 20:1, preferably from 1:15 to 15:1, more preferably 1:10 to 10:1 and incremental values in between.

If the adjuvant comprises two or more components, their relative fractions may also vary. Thus, for example, the weight ratio of components (iv) and (v) or the weight ratio of components (iv) and (vi) and or the weight ratio of components (v) and (vi) may be in the range from 1:20 to 20:1, preferably from 1:15 to 15:1, more preferably 1:10 to 10:1, and may comprise incremental values in between.

In a preferred embodiment, the particulate composition of the invention is substantially free from formaldehyde. The expression "substantially free from formaldehyde" in the sense of the present invention means that the composition includes <0.1 wt %, preferably <0.05 wt %, more preferably <0.005 wt % and even more preferably <0 0005 wt % of formaldehyde.

A further aspect of the present invention relates to the use of an additive and/or of an adjuvant as described above for producing a particulate composition comprising urea.

All preferred embodiments which have been described above in connection with the particulate composition of the invention are also valid correspondingly for the inventive use of the additive and/or of the adjuvant for producing a particulate composition comprising urea, and will not be repeated at this point, therefore.

A further aspect of the invention relates to a method for producing a particulate composition comprising urea, comprising the steps of
(A) providing a urea-containing solution;
(B) granulating of the urea-containing solution in a fluidized bed, in a granulating drum or on a granulating plate, or prilling the urea-containing solution, in each case with addition of an additive and/or of an adjuvant with a composition as described above.

All preferred embodiments described above in connection with the particulate composition of the invention are also valid correspondingly for the method of the invention for producing a particulate composition comprising urea, and will not be repeated at this point, therefore.

In one preferred embodiment of the method of the invention, the urea content of the solution used in step (A) is >50 wt %, preferably >60 wt %, more preferably >70 wt %, very preferably >80 wt %, more preferably still >96 wt %.

The granulating of the urea-containing solution with addition of an additive and/or of an adjuvant as per step (B) may take place by customary techniques known to the skilled person, as for example by means of spray crystallization (prilling), drum granulation or fluidized bed granulation.

In one preferred embodiment of the method of the invention, the granulating in step (B) takes place by means of granulation in a fluidized bed, in a granulating drum or on a granulating plate, or by means of prilling. The urea-containing solution is preferably granulated in step (B) by means of fluidized bed granulation, comprising the steps of:
(B1) providing urea-containing nuclei;
(B2) fluidizing the urea-containing nuclei;
(B3) spraying on the urea-containing solution, using an additive and/or an adjuvant with a composition as described above.

If the additive and/or the adjuvant comprises two or more components, each of these components may be used individually or together, or else in the form of premixes, in the method of the invention. The timings and addition of the components may vary. It is possible, for example, to add one or more of the components to the provided urea solution, or else to add one or more of the components to the urea-containing solution not until immediately before said solution is applied by spraying. Depending on the nature of the components, it may be advantageous to use the components in the form of solutions, suspensions, emulsions or the like.

Suitable liquids contemplated for the solutions or other formulations include, in particular, water, but also organic solvents such as, for example, alcohols, ethers, etc.

The temperature of the urea-containing solution is preferably >120° C., more preferably 125° C. and very preferably >130° C.

In one embodiment of the invention, the method comprises step (C):

(C): separating the particulate urea composition into three fractions after it has been produced, where one fraction (F1) contains particles having the desired target size, one fraction (F2) contains particles having a size above the desired target size, and one fraction (F3) contains particles having a size below the desired target size, and where preferably the fraction F2, after comminution of the particles, and the fraction F3 are returned into the method.

In units for the preparation of urea and for the further processing thereof into particulate compositions customarily ammonia is generated. This ammonia can be scrubbed with suitable acids, such as nitric acid or sulfuric acid, for example, to convert it into the corresponding ammonium salts, such as ammonium nitrate or ammonium sulfate, for example, which can be passed on for further use, in fertilizers, for example. Suitable methods and performance of the acid scrub are described in WO2010/060535, for example.

In a further embodiment, the method of the invention comprises step (D):

(D) acid scrubbing.

The acid scrubbing may advantageously also take place with use of the above-described acids of component (iv), meaning that the salts thus obtained can then be utilized as component (iv) in the additive used in accordance with the invention.

A further aspect of the present invention relates to a particulate composition obtainable by a method of the invention as described above.

A further aspect of the present invention is the use of a particulate urea composition as described above as fertilizer.

A further aspect of the invention relates to an apparatus for producing a particulate composition comprising urea, comprising:

(a) a granulator;
(b) at least one means for adding an additive and/or an adjuvant as described above;
(c) at least one means for separating the particulate composition into fractions of different particle sizes;
(d) optionally at least one means for performing an acid scrub.

In one preferred embodiment of the apparatus of the invention, the granulator (a) is a fluidized bed granulator.

The apparatus of the invention is particularly suitable for performing the method of the invention. A further aspect of the invention therefore relates to the use of the apparatus of the invention for performing the method of the invention for producing a particulate composition comprising urea.

The methods of the invention and the apparatus of the invention can be combined, for example, with a unit for preparing urea.

In the text below, the invention is elucidated using examples. These elucidations are merely exemplary and do not confine the general concept of the invention.

EXAMPLES

Example 1

In an experimental plant, urea was granulated with 7 wt % of elemental sulfur in a fluidized bed granulator comprising a cylindrical fluidized bed with a diameter of 40 cm at a temperature of around 108° C. The fluidized bed ended on the underside with a perforated plate whose holes had a diameter of 2.0 mm. With a superficial velocity of around 2 m/s, the fluidizing air flowed into the fluidized bed. An overflow was placed 10 cm above the bottom plate on the side wall of the bed. A defined quantity (around 45 kg) of particles or granules having a narrow size distribution was then introduced as granulating nuclei into the column of the granulator. The bed with the nuclei (around 50 cm deep) was fluidized with hot air at a temperature of around 100° C., and the addition of 96 to 97 wt % strength urea solution with a temperature of around 135° C. was commenced as soon as the bed had attained the temperature of around 108° C. envisaged for the run. From a supply tank, the solution, consisting of urea and sulfur with a water content of 3-4 wt %, was then supplied at a rate of 350 kg/h via a spraying nozzle, which was operated at a temperature of around 140° C. with air supplied at a rate of 240 kg/h, into the fluidized bed granulator. The granulating additives used according to table 1 below were then mixed at around 135° C. with the solution consisting of urea and sulfur. Solids were removed from the fluidized bed via an outlet at regular intervals of 5 minutes, in order to maintain a largely constant bed height. The samples of the solids thus removed were then each sieved for determination of their size distribution. No solids were returned to the fluidized bed granulator. The duration per batch was in each case around 30 minutes. After this time had elapsed, the supply was interrupted, and the granules were cooled to around 100° C., removed from the fluidized bed granulator and sieved for separation into the various fractions. The fraction with the desired size distribution was then cooled to around 60° C. for analysis of its product properties. All fractions were weighed to determine the growth rate of the granules. Furthermore, the dust from the bag filters of the air removal apparatus was also collected and weighed.

In accordance with the procedure described above, comparative granulation experiments as well, without addition of additive and also with polyvinylamine (PVA), a polyvinylamine/polyethyleneimine mixture or a standard additive (urea-formaldehyde additive UF80), were carried out and the granules obtained in each case were worked up accordingly and analyzed.

Table 1 below shows the corresponding assessment of the granules in relation to dusting, compressive strength, density and caking. The dusting sensitivity, which is likewise reported, is the result of a visual assessment of captured dust from a small fluidized bed condenser. The scale used for the evaluation of the granules obtained is shown in table 1b.

Suitable analytical methods for the product properties are known to the skilled person. Reference may be made, for example, to ISO 3944 or IFDC S-112 for determining the bulk density, to IFDC S-116 for determining the dusting, to IFDC S-115 for determining the compressive strength, and to IFDC S-106 for determining the caking, the IFDC techniques being those of the International Fertilizer Development Center, Muscle Shoals, Ala., USA.

TABLE 1

| | | — | UF80 | PVA/PEI 88/12 | PVA/PEI/ PVAl 44/6/50 | PVA/PEI/ CA 34.5/3.5/62 | PVA/PEI/ PVAl/CA 17.2/1.8/50/31 | PVA/PEI/ CA 80/10/10 |
|---|---|---|---|---|---|---|---|---|
| Inventive (E)/ comparative (V) | | V | V | E | E | E | E | E |
| Amount added mg/kg | | 0 | 3000 | 1000 | 2000 | 2000 | 2000 | 1000 |
| Parameter | good means | | | | | | | |
| Dust in granulator filter | low | 5 | 2 | 2 | 2 | 1 | 2 | 2 |
| Dusting cooling | low | 5 | 2 | 2 | 2 | 1 | 2 | 2 |
| Caking % | none | 3 | 1 | 1 | 1 | 1 | 1 | 1 |
| Lump hardness | FF* | 3 | 1 | 1 | 1 | 1 | 1 | 1 |
| Compressive strength | high | 4 | 2 | 2 | 2 | 1 | 2 | 2 |
| Bulk density (loose) | high | 3 | 1 | 1 | 2 | 1 | 1 | 1 |
| Assessment (unweighted) | | 23 | 9 | 9 | 10 | 6 | 9 | 9 |

PVA: polyvinylamine
PEI: polyethyleneimine
PVAl polyvinyl alcohol
CA citric acid
FF free flowing

TABLE 2

| Scale | Dust in the filter (%) | Dust cooling | Compressive strength kg | Bulk density (g/l) | Caking (%) | Hardness (kg) |
|---|---|---|---|---|---|---|
| 1 | 0-4 | 0 | >3.5 | >675 | 0 | none |
| 2 | >4-6 | 1 | >3.0-3.5 | 675-665 | 0-10 | slight |
| 3 | >6-8 | 2 | >2.5-3.0 | <665-655 | 11-20 | moderate |
| 4 | >8-10 | 2-3 | >2.0-2.5 | <655-645 | 21-30 | hard |
| 5 | >10 | 3 | <2.0 | <645 | >30 | |

Example 2

In accordance with the procedure described in example 1, the effect was determined of a granulating additive of the invention composed of citric acid in various dosages and mixtures of polyethyleneiminine and polyvinylamine. In this case the citric acid was supplied as a mixture of polyethyleneiminine/polyvinylamine and in dosed form to the stream of urea and sulfur that was supplied to the nozzle, prior to spraying. The resulting solution, consisting of urea and sulfur with a water content of 3 wt %, was then supplied at a rate of 350 kg/h at a temperature of 132° C., and working up took place as described in example 1. A corresponding comparative experiment with formaldehyde was likewise performed.

Table 1 shows in each case the fraction of dust in the fluidized bed granulator, and also gives the corresponding assessment of the granules of example 2.

Example 3

In accordance with the procedure described in example 1, the effect was determined of granulating additives of the invention, consisting of a mixture of 500 mg/kg polyethyleneiminine and polyvinylamine (40 wt %/60 wt %, based in each case on the mixture of polyethyleneimine and polyvinylamine) with oxalic acid, citric acid, succinic acid, phthalic acid, phthalic anhydride, glutaraldehyde and also glyoxylic acid, on the granulation of urea and ammonium sulfate. Oxalic acid, citric acid, succinic acid, phthalic acid, phthalic anhydride and glutaraldehyde were each added to the urea reservoir, and the glyoxylic acid and also the mixture of polyethyleneiminine and polyvinylamine were each added, prior to spraying, to the solution consisting of urea and ammonium sulfate that was supplied to the nozzle. Here again, the solution thus obtained with a water content of 3 wt % was then supplied at a rate of 350 kg/h at a temperature of 132° C., and working up took place as described in example 1. A corresponding comparative experiment with formaldehyde was likewise performed.

| | Inventive (E)/ comparative (V) | Dosage (mg/kg) | Compressive strength (in kg) | Dusting (in %) |
|---|---|---|---|---|
| No additive | V | 0 | 2.26 | 10.85 |
| Formaldehyde | V | 4500 | 3.75 | 3.90 |
| Oxalic acid | E | 1000 | 4.48 | 2.81 |
| Citric acid | E | 1000 | 4.05 | 4.44 |
| Succinic acid | E | 1000 | 3.63 | 3.70 |
| Phthalic acid | E | 1000 | 3.84 | 3.70 |
| Phthalic anhydride | E | 1000 | 4.72 | 2.48 |
| Glutaraldehyde | E | 1000 | 3.71 | 3.65 |
| Glyoxylic acid | E | 1500 | 5.07 | 2.74 |

The investigations of the granules obtained according to examples 1-3 showed that both dusting and the properties of the granules (compressive strength, tendency toward caking) improved when the additives of the invention were added. The result was comparable with or even better than the results obtained when using formaldehyde, while requiring substantially smaller quantities of additive.

What is claimed is:
1. A particulate composition comprising:
   (i) urea;
   and an additive comprising component (ii) and at least one of components (iii) or (vii):
   (ii) a combination of polyethyleneimine and polyvinyl alcohol, or a combination of polyethyleneimine and polyvinylamine;

(iii) at least one aliphatic $C_2$-$C_8$ dialdehyde;

(vii) at least one compound selected from the group consisting of aliphatic dicarboxylic acids, their salts and anhydrides, aliphatic tricarboxylic acids, their salts and anhydrides, aromatic dicarboxylic acids, their salts and anhydrides, and aldehydic acids, their salts and anhydrides, and an adjuvant comprising at least one of components (iv) or (v):

(iv) sulfur;

(v) ammonium sulfate;

wherein the weight fraction of component (i) is greater than 50 wt % and the weight fraction of the sum of components (ii), (iii) and (vii) in the composition is less than 1 wt % and the weight fraction of the sum of components (iv) and (v) in the composition is less than 50 wt % and the weight ratio of components (ii) and (iii) or the weight ratio of components (ii) and (vii) is in the range from 1:20 to 20:1.

2. The particulate composition of claim 1 wherein component (ii) is the combination of polyethyleneimine and polyvinylamine; component (iii) is at least one of ethanedial or glutaraldehyde; and component (vii) is selected from the group consisting of oxalic acid, succinic acid, citric acid, phthalic acid, phthalic anhydride, glyoxylic acid and salts thereof.

3. The particulate composition of claim 1 wherein the polyethyleneimine of component (ii) has a molecular weight in the range of 500-2,000,000 Da.

4. The particulate composition of claim 1 wherein component (ii) includes polyvinylamine having a molecular weight in the range of 500-1,000,000 Da.

5. The particulate composition of claim 1 wherein the weight fraction of the sum of components (ii), (iii) and (vii) in the composition is less than 0.5 wt %.

6. The particulate composition of claim 1 wherein the weight fraction of the sum of components (ii), (iii) and (vii) in the composition is less than 0.4 wt %.

7. The particulate composition of claim 1 wherein the weight fraction of the sum of components (ii), (iii) and (vii) in the composition is less than 0.3 wt %.

8. The particulate composition of claim 1 wherein the weight fraction of the sum of components (ii), (iii) and (vii) in the composition is less than 0.25 wt %.

9. A method for producing a particulate composition comprising urea, comprising the steps of:

providing a urea-containing solution; and granulating or prilling the urea-containing solution with addition of at least one of:

an additive comprising component (ii), or at least one of components (iii) or (vii):

(ii) a combination of polyethyleneimine and polyvinyl alcohol, or a combination of polyethyleneimine and polyvinylamine;

(iii) at least one aliphatic $C_2$-$C_8$ dialdehyde;

(vii) at least one compound selected from the group consisting of aliphatic dicarboxylic acids, their salts and anhydrides, aliphatic tricarboxylic acids, their salts and anhydrides, aromatic dicarboxylic acids, their salts and anhydrides, and aldehydic acids, their salts and anhydrides, and an adjuvant comprising at least one of components (iv) or (v):

(iv) sulfur;

(v) ammonium sulfate.

10. The method of claim 9 wherein the urea content of the solution is greater than 10 wt %.

11. The method of claim 9 wherein the urea content of the solution is greater than 50 wt %.

12. The method of claim 9 wherein said granulating is performed by fluidized bed granulation, comprising the steps of:

providing urea-containing nuclei;

fluidizing the urea-containing nuclei; and spraying the urea-containing solution onto the nuclei, using at least one of the additive or the adjuvant.

13. The method of claim 9 wherein the temperature of the urea-containing solution is greater than 120° C.

14. The method of claim 9 wherein the temperature of the urea-containing solution is greater than 125° C.

15. The method of claim 9 wherein the temperature of the urea-containing solution is greater than 130° C.

16. The method as claimed in claim 9, further comprising:

separating the particulate urea composition after its production into three fractions, wherein one fraction (F1) contains particles having the desired target size, one fraction (F2) contains particles having a size above the desired target size, and one fraction (F3) contains particles having a size below the desired target size.

17. The method of claim 9 further comprising:

wet scrubbing.

18. A fertilizer comprising:

a particulate urea composition comprising:

(i) urea;

and an additive comprising component (ii) and at least one of components (iii) or (vii):

(ii) a combination of polyethyleneimine and polyvinyl alcohol, or a combination of polyethyleneimine and polyvinylamine;

(iii) at least one aliphatic $C_2$-$C_8$ dialdehyde;

(vii) at least one compound selected from the group consisting of aliphatic dicarboxylic acids, their salts and anhydrides, aliphatic tricarboxylic acids, their salts and anhydrides, aromatic dicarboxylic acids, their salts and anhydrides, and aldehydic acids, their salts and anhydrides, and an adjuvant comprising at least one of components (iv) or (v):

(iv) sulfur;

(v) ammonium sulfate;

wherein the weight fraction of component (i) is greater than 50 wt % and the weight fraction of the sum of components (ii), (iii) and (vii) in the composition is less than 1 wt % and the weight fraction of the sum of components (iv) and (v) in the composition is less than 50 wt % and the weight ratio of components (ii) and (iii) or the weight ratio of components (ii) and (vii) is in the range from 1:20 to 20:1.

* * * * *